United States Patent [19]
Ferruccio et al.

[11] Patent Number: 6,020,498
[45] Date of Patent: Feb. 1, 2000

[54] PROCESS FOR PREPARING CARBOXAMIDE OXIMES

[75] Inventors: Laurence Ferruccio, Vert-le-Grand; Dominique Gibert, Villers-Sous-Saint-Leu; Guyselaine Vergne, Maisse, all of France

[73] Assignee: ISOCHEM, Paris, France

[21] Appl. No.: 09/358,816

[22] Filed: Jul. 22, 1999

[30] Foreign Application Priority Data

Aug. 4, 1998 [FR] France .................................. 98 09977

[51] Int. Cl.$^7$ ................................................. C09D 487/04
[52] U.S. Cl. ...................................................... 548/371.7
[58] Field of Search ........................................ 548/371.7

[56] References Cited

U.S. PATENT DOCUMENTS 4,705,863 11/1987 Sato et al. .

FOREIGN PATENT DOCUMENTS 0 571 959  12/1993  European Pat. Off. .
7-082252   3/1995   Japan .
9-278758   10/1997  Japan .

OTHER PUBLICATIONS

Kimura etal, Chemical Abstracts, vol. 114, No. 64267, 1991.

*Primary Examiner*—Robert W Ramsuer
*Attorney, Agent, or Firm*—Oliff & Berridge, PLC

[57] ABSTRACT

The invention relates to a process for preparing carboxamide oximes of the formula (I):

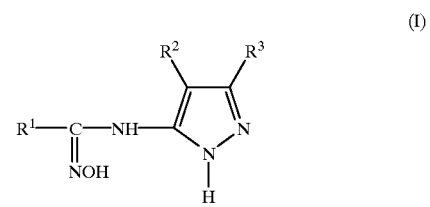

in which $R^1$ represents an aryl or heteroaromatic group, and $R^2$ and $R^3$ represent a hydrogen atom or groups as defined in the description, characterized by the three following steps:

1) An amide of the formula (II) $R^1CONHR^4$, with $R^1$ having the previous meaning and $R^4$ being a $C_1$ to $C_8$ alkyl group, is reacted with a chlorinating agent in order to obtain the corresponding chloroimine,
2) The resulting chloroimine is then caused to react with an aminopyrazole in order to obtain a novel disubstituted amidine,
3) The resulting amidine is caused to react with hydroxylamine or one of its salts.

Carboxamide oximes are prepared more rapidly, and in a good yield, in this way. They are useful as synthesis intermediates, in particular for preparing photographic developing agents.

16 Claims, No Drawings

PROCESS FOR PREPARING CARBOXAMIDE OXIMES

The invention relates to a novel process for preparing carboxamide oximes. In particular, it relates to a process for preparing N-pyrazolyl-substituted carboxamide oximes (with carboxamide oximes also being termed amidoximes), and to the novel amidine intermediates.

N-pyrazolyl-substituted carboxamide oximes are compounds which are known to be useful as synthesis intermediates, in particular for producing photographic developing agents or pharmaceutical products.

Several processes have been proposed for preparing them. One of them involves the four following steps:

in the first step, a carboxamide, which is not substituted on the nitrogen, is caused to react with a dehydrating agent, such as phosphorus oxychloride, in order to obtain the corresponding nitrile, in the second step, the resulting nitrile is reacted with an alcohol, in an acidic or basic medium, in order to obtain an imidate, in the third step, the imidate is reacted with an aminopyrazole in order to obtain an amidine which is mono-substituted on a nitrogen atom, in the fourth step, the monosubstituted amidine is reacted with hydroxylamine in order to obtain the amidoxime sought.

The reaction scheme is as follows:

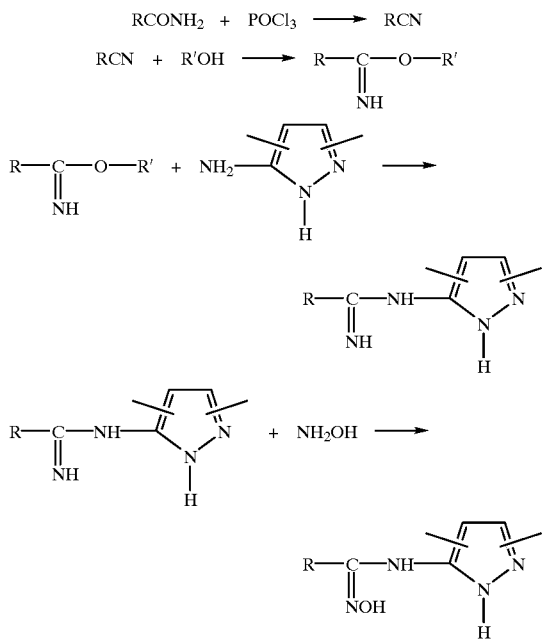

This process suffers from drawbacks. Four steps are required starting from the amide. Of these steps, the transformation of the amide into a nitrile is a particularly tricky operation. Nitriles, in particular aromatic nitrites, are toxic compounds. Some are, in particular, methaemoglobin-forming agents. They have to be handled with a great deal of caution and they should be removed from the effluents before the latter are discharged. In general, the reaction is carried out using phosphorus oxychloride, frequently in excess. The resulting nitrile is contaminated with by-products, in particular with phosphorus-containing derivatives. A large number of washes are then necessary in order to remove the excess of phosphorus oxychloride and the phosphorus-containing by-products. This consequently results in a large quantity of effluents. Some of the nitrile is entrained by these effluents, which then have to be treated.

Another process, which is described in the U.S. Pat. No. 4,705,863, consists in causing an aminopyrazole to react with an orthoester in order to obtain an imidoester. The latter is then caused to react with hydroxylamine in order to obtain the carboxamide oxime sought.

This process also suffers from drawbacks. The preparation of the orthoesters poses problems. It is carried out in two steps, either passing by way of a nitrile intermediate, with the same disadvantages as previously pointed out, or by means of chlorinating an $RCH_3$ derivative in order to obtain the trichlorinated intermediate $RCCl_3$, which is reacted with an alcohol. However, the trichlorinated derivatives also possess toxic and irritant properties. They are furthermore always obtained in a mixture with other chlorinated derivatives. The reaction with alcohol also leads to mixtures of alkylated derivatives.

The reaction scheme is as follows:

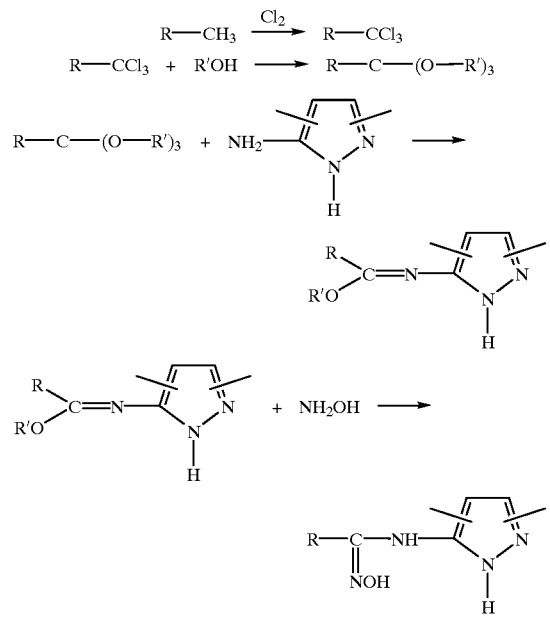

Consequently, four steps are also required in order to obtain carboxamide oximes from common raw materials.

The invention relates to a process for preparing N-pyrazolyl-substituted carboxamide oximes, which process does not suffer from the drawbacks of the previous processes and involves fewer steps to be carried out from readily available starting materials.

The process according to the invention consists in preparing N-pyrazolyl-substituted carboxamide oximes of the formula (I):

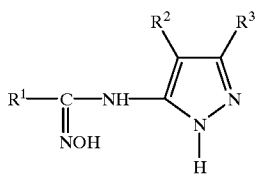

(I)

in which
R¹ represents a substituted or unsubstituted aryl group, or a substituted or unsubstituted heteroaromatic group,
R² represents a hydrogen atom, a halogen atom or a substituted or unsubstituted aryloxy group, and
R³ represents a hydrogen atom, a halogen atom, a hydroxyl group, a cyano group, a nitro group, a carboxyl group, a substituted amino group, or a substituted or unsubstituted alkyl, cycloalkyl, aralkyl, aryl, heteroaromatic, alkoxy, aryloxy, acyl, acylamino, sulphonylamino, sulphonyl, alkylthio, arylthio, carbamoyl, sulphamoyl or ureido group, by means of the following steps:

1) An amide, represented by the formula R¹CONHR⁴ (II), in which R¹ has the previously indicated meaning and R⁴ represents a $C_1$ to $C_8$ alkyl group, is first of all caused to react with a chlorinating agent, where appropriate in the presence of an inert solvent, in order to obtain the corresponding chloroimine, which is represented by the formula (III)

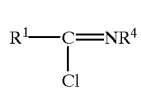

(III)

2) The resulting chloroimine is then caused to react with an aminopyrazole which is represented by the formula (IV)

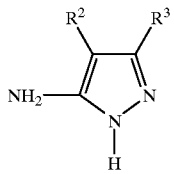

(IV)

in which R² and R³ have the previously indicated meanings, where appropriate in the presence of an inert solvent, in order to obtain a novel amidine whose two nitrogen atoms carry a substituent, as represented by the formula (V)

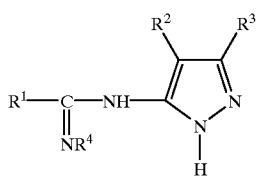

(V)

in which R¹, R², R³ and R⁴ have the previously indicated meanings.

3) The resulting amidine is caused to react with hydroxylamine or one of its salts, where appropriate in the presence of an inert solvent.

The reaction scheme is as follows:

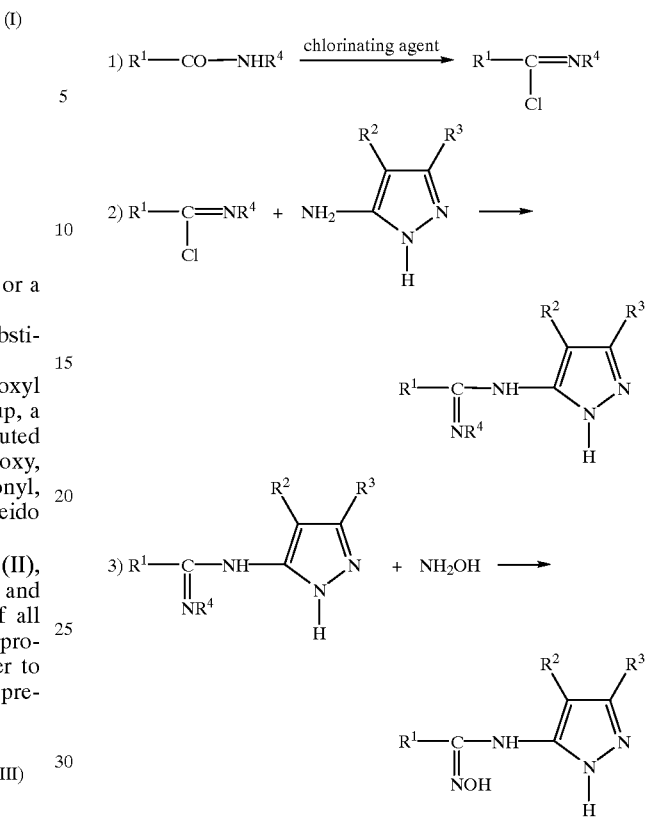

The novel process according to the invention is particularly advantageous. It only involves three steps. The carboxamide oximes are consequently obtained more rapidly, with this being even more the case since the first two steps are of a shorter duration than are those of the previous processes. In none of the steps is there any formation of a nitrile or trichlorinated intermediate, which are very toxic compounds.

In the compounds of the formula (I), (II), (III) and (V), the substituents of R¹, which represents an aryl or heteroaromatic group, are groups which are inert under the reaction conditions employed and are in general selected from the group consisting of halogen atoms, namely fluorine, chlorine, bromine or iodine atoms, linear or branched, $C_1$ to C8 alkyl groups which are unsubstituted or substituted, in particular by halogen atoms, such as, in particular, the $CF_3$ group, substituted or unsubstituted $C_1$ to $C_8$ alkyloxy groups, substituted or unsubstituted aryloxy groups, the nitro group, or substituted or unsubstituted aryl or heteroaromatic groups. All the hydrocarbon groups of the substituents of R¹ can themselves be substituted by the substituents which are indicated in this paragraph.

The aryl group which R¹ represents is generally a phenyl or naphthyl group. Preferably R¹ represents the 4-nitrophenyl group.

When R¹ represents a heteroaromatic group, this latter can contain one or more heteroatoms such as oxygen, sulphur or nitrogen and is, for example, furan, thiophene, pyridine or pyrimidine.

The radical R², which is carried by the pyrazole ring in the compounds of the formula (I), (IV) and (V), represents a hydrogen atom, a halogen atom, namely a fluorine, chlorine, bromine or iodine atom, preferably a chlorine atom, or an aryloxy group which is unsubstituted or substituted by the substituents which are described above for the $R^1$ group. $R^2$ preferably represents a hydrogen atom.

The radical $R^3$, which is the other radical which is carried by the pyrazole ring in the compounds of the formula (I), (IV) and (V), can have a large number of meanings and can, in particular, represent a hydrogen atom, a halogen atom, a hydroxyl group, a nitro group, a carboxyl group, a cyano group, a substituted amino group, a primary, secondary or tertiary $C_1$ to $C_{22}$ alkyl group, such as the methyl, ethyl, propyl, isopropyl, butyl, isobutyl, tert-butyl, tert-amyl, pentyl, hexyl, heptyl, octyl, decyl, undecyl, tridecyl or octadecyl group, or a cycloalkyl, aralkyl, aryl or heteroaromatic group. $R^3$ can also represent an alkoxy, in particular $C_1$ to $C_4$ alkoxy, aryloxy, acyl, acylamino, sulphonylamino, sulphonyl, alkylthio, arylthio, carbamoyl, sulphamoyl or ureido group.

All the hydrocarbon groups contained in the groups represented by $R^3$ can themselves be substituted by the groups indicated in this definition of $R^3$.

$R^3$ is preferably a substituted or unsubstituted $C_1$ to $C_4$ alkyl group, more especially a tertiary alkyl group such as the tert-butyl group.

The radical $R^4$, which is contained in the starting amide of the formula (II), and which is found once again in the compounds of the formula (III) and (V), is a $C_1$ to $C_8$, preferably $C_1$ to $C_4$, alkyl group, such as the methyl, ethyl, propyl or butyl group. $R^4$ preferably represents the methyl or ethyl group.

The three steps of the process will be described below in more detail. In this description (not including the examples) and in the corresponding claims, all the numbers expressing quantities of compounds or reaction conditions should be understood as being preceded by the term "about".

In order to carry out step 1), use is generally made of a chlorinating agent such as, in particular, thionyl chloride ($SOCl_2$), phosphorus pentachloride ($PCl_5$), phosphorus oxychloride ($POCl_3$), or phosgene ($COCl_2$), or one of their mixtures. Preference is given to using thionyl chloride.

The starting amide of the formula (II) is a compound which can be obtained commercially or which can be prepared using known methods, for example from an acyl halide and an amine.

The chlorinating agent is employed in stoichiometric quantity or in excess. For reasons of economy, the quantity of chlorinating agent is preferably from 1 to 1.25 mol per mole of amide.

The reaction can be carried out without solvent, with the chlorinating agent then serving as the solvent, or in the presence of a solvent or a mixture of solvents which are inert under the reaction onditions and which are selected from chlorinated or unchlorinated aromatic hydrocarbons such as toluene, the xylenes, monochlorobenzene or the dichlorobenzenes, or chlorinated or unchlorinated aliphatic hydrocarbons such as ethane or dichloromethane. Toluene is very suitable.

The temperature of the reaction is generally between 25° C. and the reflux temperature of the solvent. When toluene is the chosen solvent and the chlorinating agent is thionyl chloride, the temperature is, in particular, between 70° C. and 110° C.

Catalysts such as N,N-dialkylated amides, in particular dialkylated formamides whose alkyl groups possess from 1 to 8 carbon atoms, such as N,N-dimethylformamide and, more especially, N,N-dibutylformamimde, can be added in order to accelerate the reaction.

In general, the chlorination lasts between 2 and 15 hours. Once the reaction has finished, it is not necessary to isolate the chloroimine which is formed from the reaction medium.

In order to carry out step 2), the aminopyrazole of the formula (IV) is then caused to react with the chloroimine which has been obtained. The aminopyrazole employed is a compound which is available commercially or which is prepared using known methods.

The quantity of the aminopyrazole employed is generally the stoichiometric quantity or an excess, with this excess being, in particular, an excess which can extend to 0.5 mol per mole of chloroimine. For reasons of cost, preference is given to using from 1 to 1.25 mol of aminopyrazole per mole of chloroimine.

The reaction is generally carried out in the presence of a solvent, or of a mixture of solvents, which are inert under the reaction conditions and which are selected from $C_1$ to $C_8$ aliphatic alcohols, chlorinated or unchlorinated aromatic hydrocarbons, such as toluene, the xylenes, monochlorobenzene or the dichlorobenzenes, chlorinated or unchlorinated aliphatic hydrocarbons, ethers, such as tetrahydrofuran, or esters such as ethyl acetate or isopropyl acetate. Preference is given to using alcohols, in particular methanol and/or isopropanol.

The reaction is exothermic and the reaction medium is generally maintained at a temperature ranging from −10° C. to +30° C., preferably between 0° C. and 15° C. in order to avoid side reactions.

While it is possible to neutralize the hydrochloric acid which is formed, by adding a base, such as triethylamine, sodium acetate or pyridine, this is not a preferred variant.

The process according to the invention makes it possible to obtain the amidines of the formula (V), which are novel compounds. It was found, unexpectedly, that the amine function which is substituted on the pyrazole ring is the reactive function which attaches to the carbon of the chloroimine. Thus, it could have been expected that one of the nitrogens of the ring would be more reactive or would react competitively, as in other reactions of the prior art using these same pyrazoles, and that a mixture of amidines would be obtained. The amidines of the formula (V) are generally formed as the two reagents are brought into contact. In general, the reaction lasts for from 2 to 10 hours.

When the reaction has finished, it is not necessary, either, to carry out a prior isolation of the resulting amidine, since the third step of the process can be performed in the same solvents as previously indicated. The hydroxylamine, or one of its salts, such as a hydrochloride or a sulphate, is then preferably added directly to the reaction medium. When hydroxylamine hydrochloride is used, the reaction is preferably carried out in the presence of a solvent which renders it soluble, such as a lower alcohol, in particular methanol. A base which releases the hydroxylamine from its salt is preferably also added in order to obtain a more complete reaction. Bases such as tertiary amines, for example triethylamine or pyridine, can be used. Preference is given to using sodium acetate.

The hydroxylamine, or its salt, is reacted with the amidine in stoichiometric quantity or in an excess, in particular an excess of from 0.5 to 2 mol per mole of amidine. Due to the toxicity of the hydroxylamine, and for reasons of economy, preference is given to using a quantity of from 1.5 to 2 mol of hydroxylamine per mole of amidine.

The temperature of the reaction is generally between 0° C. and 60° C., preferably between 35° C. and 45° C. The duration of the reaction is generally from 2 to 10 hours.

Surprisingly, the desired amidoxime, that is the amidoxime containing the pyrazolyl radical, is formed in an excellent yield. The amine of the formula $R^4NH_2$ is formed at the same time. Given that the two nitrogen groups of the amidine molecule of the formula (V) are both substituted and that they can both be leaving groups, it was to be feared that the reaction would take place with the loss of the aminopyrazole part or that a mixture of several amidoximes would be obtained. This is not the case.

The amidoxime which is formed can be recovered using standard methods, for example by removing the solvents, filtration, washing with water and drying.

The amidoximes are obtained in accordance with the process of the invention at a high level of purity and in an excellent yield, with the yield of each of the steps being greater than 90%. In particular, when the $R^1$ group of the starting amide is the 4-nitrophenyl radical and the aminopyrazole is the 3-tert-butyl-5-aminopyrazole, the amidoxime is obtained with yields of from 75 to 90%, and its purity is often greater than 97%. The different steps of the process are each more rapid than those employed in the prior art, and the number of steps is reduced. The process can be carried out as a "one-pot process" without isolating the intermediates. These intermediates are not toxic. The process according to the invention is consequently more advantageous than the previous processes.

The carboxamide oximes which are formed are known compounds which can be transformed in order to form compounds which are useful, in particular, as couplers for photography, sensitive dyes or pharmaceutical products.

The examples which follow illustrate the invention without, however, limiting it.

In Examples 1 to 3, N-(3-tert-butyl-5-pyrazolyl)-4-nitrobenzamide oxime of the formula

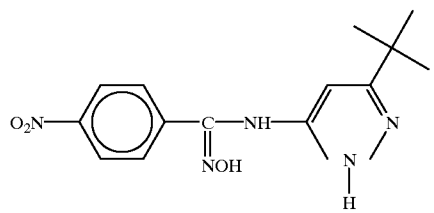

is prepared from various 4-nitrobenzamides.

EXAMPLE 1

Preparation from N-methyl-4-nitrobenzamide 9 g of N-methyl-4-nitrobenzamide and 40 g of thionyl chloride are introduced into a 100 ml three-necked flask which is fitted with a stirrer. The mixture is heated gradually up to the reflux temperature of the thionyl chloride. The initially heterogeneous medium becomes homogeneous. An evolution of gas occurs from 65° C. onwards and is maintained until the medium becomes completely homogeneous. It stops approximately 1 hour after the start of the heating.

The reaction mixture is kept for a further 1 hour with the thionyl chloride refluxing.

The excess of thionyl chloride is removed by distillation under atmospheric pressure or under reduced pressure (50 mmHg) until a mixture temperature of 85°–95° C. is obtained.

10 g of toluene are then added to the reaction mixture, after which distillation of the excess thionyl chloride is completed by distilling off the larger part of the toluene. A further 10 g of toluene are then added and the reaction mixture is cooled down to +3° C. The chloroimine derivative precipitates around 45° C.

A solution of 6.9 g of 3-tert-butyl-5-aminopyrazole in 14 g of isopropanol is introduced, over 1 hour, while at the same time maintaining the temperature between +5° C. and +15° C.

The medium thickens considerably and becomes orange-coloured. 20 ml of isopropyl alcohol are then added in order to improve the stirrability of the medium.

Stirring of the mixture is continued, at 20°–30° C., for 2 hours.

Monitoring by thin layer chromatography (TLC) shows the disappearance of the aminopyrazole and the appearance of the amidine.

20 ml of methanol are then added, followed by 7.2 g of hydroxylamine hydrochloride. The methanol is used to render the medium fluid and promotes solubilization of the hydroxylamine hydrochloride. The reaction medium is heated to 40°–50° C., after which 3.9 g of sodium acetate are added. The medium thickens considerably and then effloresces while becoming lemon-yellow coloured.

The heating of the reaction medium is continued for 4 hours. The disappearance of the amidine is monitored by TLC.

When all the amidine has disappeared, the mixture of solvents is expelled by distillation under reduced pressure (50 mmHg) until a pasty lemon-yellow coloured medium is obtained. 50 ml of deionized water, which has been heated to 50° C., are slowly introduced onto the concentrate, which is maintained at 40°–45° C.

The expected amidoxime precipitates as the water is introduced. The mixture continues to be stirred, at 40°–45° C., for 1 hour.

The precipitate is harvested by filtration and is then rinsed with approximately 100 ml of water at 50° C.; the lemon-yellow coloured solid is then dried in an oven.

This results in 12.6 g of the amidoxime, whose purity is 95%, as determined by TLC, and 96%, as determined by $^1$H NMR. Taking these determinations into account, the resulting yield is 80% of pure amidoxime, based on the starting amide.

EXAMPLE 2

Preparation from N-ethyl-4-nitrobenzamide 45 kg of moist N-ethyl-4-nitrobenzamide (164.1 mol), 65 kg of toluene and 590 g (3.45 mol) of N,N-dibutylformamide are introduced, under a nitrogen atmosphere, into a 250 l enamel reactor which has been blanketed with nitrogen. The mixture is heated to 85° C., after which 37.2 kg (311 mol) of thionyl chloride are introduced, over a period of 1 hour and 45 minutes, while maintaining the mixture in the vicinity of this temperature. The mixture gradually becomes homogeneous. Hydrochloric acid and sulphur dioxide are emitted. Stirring of the mixture is continued at 85° C. for 2 hours, after which it is cooled down. The excess of thionyl chloride is removed by distilling the toluene. Once the distillation has finished, the chloroimine derivative and toluene remain in the reactor at a 50/50 concentration by weight.

The reaction medium is cooled down to 5° C., after which 80 kg (172.5 mol) of a 30% solution of 3-tert-butyl-5-aminopyrazole in isopropanol is added to the reactor. The reaction is exothermic and lasts for 5 hours, with the medium thickening and becoming orange-coloured. Stirring is continued at a temperature of 3° C. for 1 hour and 30 minutes.

The reaction medium is reheated to 20° C. and 55 kg of methanol are then added. 24 kg (345 mol) of hydroxylamine hydrochloride are subsequently added and the reaction medium is heated to 45° C. 17 kg (207 mol) of sodium acetate are added and the heating is continued for 6 hours. The major portion of the solvents is removed by distillation under reduced pressure. The yellow-coloured reaction medium becomes viscous. 175 kg of distilled water are added at 65° C. The amidoxime gradually precipitates. The reaction medium is coloured orange/ochre. Stirring is continued at 45° C. for 1 hour. Filtering, rinsing with water and then drying results in 38.3 kg of the expected amidoxime, which is 98% pure as determined by TLC, signifying a yield of 77% based on the starting benzamide.

EXAMPLE 3

Preparation from N-propyl-4-nitrobenzamide

The procedure is as described in Example 2 but using 20.8 g of N-propyl-4-nitrobenzamide, with the other constituents being in the same molar proportions, and using a reactor and operational conditions which are suited to these quantities.

24.8 g (yield, 82%) of the expected amidoxime, which is of 97% purity (by $^1$H NMR), are obtained.

The experiment is repeated while isolating the amidine intermediate (N-propyl,N'-(3-tert-butyl-5-pyrazolyl)-4-nitrobenzamidine) in the form of its hydrochloride, which compound exhibits the following characteristics:

$^1$H NMR spectrum (DMSO, 200 MHz), δ (ppm): 1 (3H, t), 1.35 (9H, s), 1.7 (2H, m), 3.35 (2H, m) 6.15 (1H, s), 7.95 (H of NH, s), 8.02 (2H, d), 8.47 (2H, d), 11.22 (1H, broad s), 12.95 (1H, broad s).

We claim:

1. Process for preparing carboxamide oximes represented by the general formula

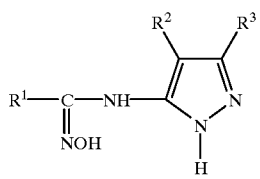

(I)

in which
- $R^1$ represents a substituted or unsubstituted aryl group, or a substituted or unsubstituted heteroaromatic group,
- $R^2$ represents a hydrogen atom, a halogen atom or a substituted or unsubstituted aryloxy group, and
- $R^3$ represents a hydrogen atom, a halogen atom, a hydroxyl group, a cyano group, a nitro group, a carboxyl group, a substituted amino group, or a substituted or unsubstituted alkyl, cycloalkyl, aralkyl, aryl, heteroaromatic, alkoxy, aryloxy, acyl, acylamino, sulphonylamino, sulphonyl, alkylthio, arylthio, carbamoyl, sulphamoyl or ureido group, characterized by the following steps:
  1) An amide, represented by the formula $R^1CONHR^4$ (II), in which $R^1$ has the previously indicated meaning and $R^4$ represents a $C_1$ to $C_8$ alkyl group, is first of all caused to react with a chlorinating agent, where appropriate in the presence of an inert solvent, in order to obtain the corresponding chloroimine, which is represented by the formula (III)

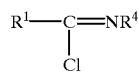

(III)

2) The resulting chloroimine is then caused to react with an aminopyrazole which is represented by the formula (IV)

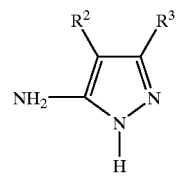

(IV)

in which $R^2$ and $R^3$ have the previously indicated meanings, where appropriate in the presence of an inert solvent, in order to obtain an amidine as represented by the formula (V)

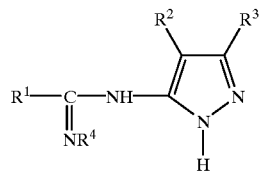

(V)

in which $R^1$, $R^2$, $R^3$ and $R^4$ have the previously indicated meanings;
  3) The resulting amidine is caused to react with hydroxylamine or one of its salts, where appropriate in the presence of an inert solvent.

2. Process according to claim 1, characterized in that the substituents of $R^1$ are selected from the group consisting of halogen atoms, linear or branched, substituted or unsubstituted $C_1$ to $C_8$ alkyl groups, substituted or unsubstituted $C_1$ to $C_8$ alkoxy groups, substituted or unsubstituted aryloxy groups, the nitro group, or substituted or unsubstituted aryl or heteroaromatic groups.

3. Process according to claim 1, characterized in that $R^1$ represents the 4-nitrophenyl group, $R^2$ represents a hydrogen atom and $R^3$ represents the tert-butyl group.

4. Process according to claim 1, characterized in that step 1) is carried out using a stoichiometric quantity or an excess of a chlorinating agent which is selected from the group consisting of thionyl chloride, phosphorus pentachloride, phosphorus oxychloride and phosgene, or one of their mixtures, at a temperature of between approximately 25° C. and the reflux temperature of the solvent.

5. Process according to claim 4, characterized in that the chlorinating agent is thionyl chloride.

6. Process according to claim 5, characterized in that the reaction is carried out in the presence of a catalyst which is selected from the N,N-dialkylated amides.

7. Process according to claim 1, characterized in that the solvent for step 1) is selected from the group consisting of the chlorinating agent, chlorinated or unchlorinated aromatic hydrocarbons and chlorinated or unchlorinated aliphatic hydrocarbons.

8. Process according to claim 1, characterized in that, in step 2), the aminopyrazole is reacted with the chloroimine, in stoichiometric quantity or in excess, at a temperature ranging from −10° C. to +30° C.

9. Process according to claim 1, characterized in that step 2) is carried out in the presence of a solvent which is selected from the group consisting of $C_1$ to $C_8$ aliphatic alcohols, chlorinated or unchlorinated aromatic hydrocarbons, chlorinated or unchlorinated aliphatic hydrocarbons, ethers and esters.

10. Process according to claim 9, characterized in that the reaction is carried out in the presence of an alcohol.

11. Process according to claim 1, characterized in that, in step 3), hydroxylamine, or one of its salts, is caused to react, in stoichiometric quantity or in excess, at a temperature ranging from 0° C. to 60° C.

12. Process according to claim 1, characterized in that, in step 3), hydroxylamine hydrochloride is caused to react in the presence of a lower alcohol and a base.

13. Process according to claim 1, characterized in that the chloroimine and the amidine which are respectively obtained in steps 1) and 2) are not isolated.

14. Amidines represented by the general formula (V)

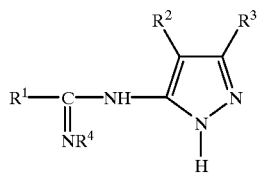

(V)

in which
- $R^1$ represents a substituted or unsubstituted aryl group, or a substituted or unsubstituted heteroaromatic group,
- $R^2$ represents a hydrogen atom, a halogen atom or a substituted or unsubstituted aryloxy group, and
- $R^3$ represents a hydrogen atom, a halogen atom, a hydroxyl group, a cyano group, a nitro group, a carboxyl group, a substituted amino group, or a substituted or unsubstituted alkyl, cycloalkyl, aralkyl, aryl, heteroaromatic, alkoxy, aryloxy, acyl, acylamino, sulphonylamino, sulphonyl, alkylthio, arylthio, carbamoyl, sulphamoyl or ureido group and
- $R^4$ represents a $C_1$ to $C_8$ alkyl group.

15. Amidines according to claim 14, characterized in that $R^1$ represents a substituted or unsubstituted aryl group, $R^2$ represents a hydrogen atom and $R^3$ represents a hydrogen atom or a $C_1$ to $C_{22}$ alkyl group.

16. Process for preparing amidines of the formula (V)

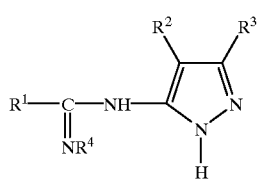

(V)

in which $R^1$ represents a substituted or unsubstituted aryl group, or a substituted or unsubstituted heteroaromatic group, $R^2$ represents a hydrogen atom, a halogen atom or a substituted or unsubstituted aryloxy group, $R^3$ represents a hydrogen atom, a halogen atom, a hydroxyl group, a cyano group, a nitro group, a carboxyl group, a substituted amino group, or a substituted or unsubstituted alkyl, cycloalkyl, aralkyl, aryl, heteroaromatic, alkoxy, aryloxy, acyl, acylamino, sulphonylamino, sulphonyl, allylthio, arylthio, carbamoyl, sulphamoyl or ureido group and $R^4$ represents a $C_1$ to $C_8$ alkyl group, characterized in that:
1) An amide. represented by the formula $R^1$ $CONHR^4$ (in which $R^1$ has the previously indicated meaning and $R^4$ represents a $C_1$ to $C_8$ alkyl group, is first of all caused to react with a chlorinating agent, where appropriate in the presence of an inert solvent, in order to obtain the corresponding chloroimine, which is represented by the formula (III)

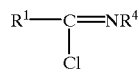

(III)

2) The resulting chloroimine is then caused to react with an aminopyrazole which is represented by the formula (IV)

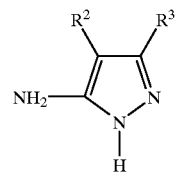

(IV)

in which $R^2$ and $R^3$ have the previously indicated meanings, where appropriate in the presence of an inert solvent, in order to obtain an amidine as represented by the formula (V)

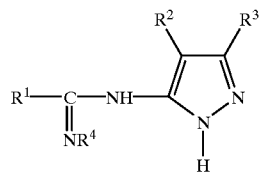

(V)

in which $R^1$, $R^2$, $R^3$, and $R^4$ have the previously indicated meanings.

* * * * *